United States Patent [19]

Drake, Jr. et al.

[11] 3,948,263

[45] Apr. 6, 1976

[54] BALLISTIC ANIMAL IMPLANT

[75] Inventors: James F. Drake, Jr., Minneapolis; Fred R. Paul, Jr., Burnsville, both of Minn.

[73] Assignee: Minnesota Mining and Manufacturing Company, St. Paul, Minn.

[22] Filed: Aug. 14, 1974

[21] Appl. No.: 497,462

[52] U.S. Cl. .................................. 128/260; 102/92

[51] Int. Cl.$^2$ .................... A61M 31/00; F42B 11/30

[58] Field of Search ........... 128/260, 268, 271, 217; 102/92 R, 92.7

[56] References Cited
UNITED STATES PATENTS

| | | | |
|---|---|---|---|
| 251,355 | 12/1881 | Gibbs | 128/271 |
| 979,993 | 12/1910 | O'Byrne et al. | 102/92 R |
| 2,617,359 | 11/1952 | Van Horn et al. | 102/92 R |
| 2,923,243 | 2/1960 | Crockford et al. | 102/92 R |
| 3,122,475 | 2/1964 | Schaeppi | 128/271 |
| 3,344,711 | 10/1967 | Mawhinney et al. | 102/92.4 |
| 3,429,263 | 2/1969 | Snyder et al. | 102/92 R |
| 3,545,439 | 12/1970 | Duncan | 128/260 |
| 3,616,758 | 11/1971 | Komarov | 102/92 R |
| 3,742,951 | 7/1973 | Zaffaroni | 128/268 |
| 3,811,444 | 5/1974 | Heller | 128/260 |
| 3,857,932 | 12/1974 | Shepherd | 128/260 X |

OTHER PUBLICATIONS

U.S. Dept. of Agriculture Paper on Ballistic Delivery of Biological Reagents by Sensory Systems Laboratory, Howard A. Baldwin, Principal Investigator, Sept. 15, 1973 18 pages.

*Primary Examiner*—Aldrich F. Medbery
*Attorney, Agent, or Firm*—Alexander, Sell, Steldt & DeLaHunt

[57] ABSTRACT

Ballistically implantable projectile adapted to carry biologically active materials into a living animal body and thereafter to provide sustained release of said biologically active material into said living animal body.

8 Claims, 5 Drawing Figures

U.S. Patent    April 6, 1976    3,948,263
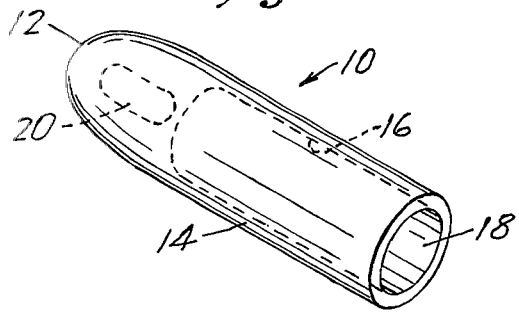
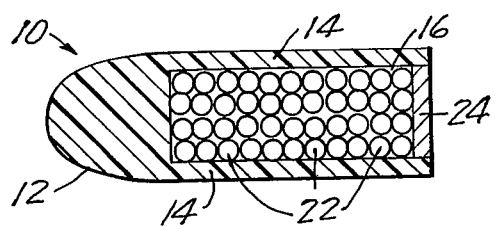
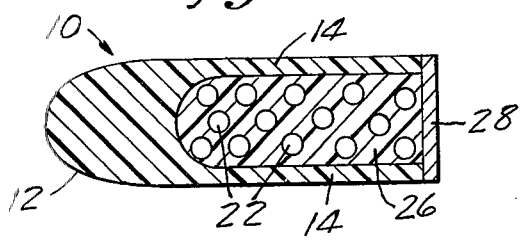
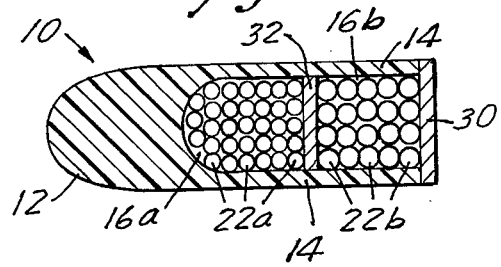
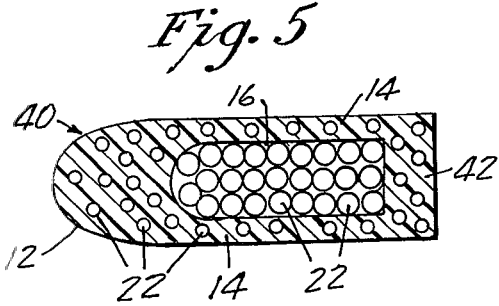

BALLISTIC ANIMAL IMPLANT

The present invention relates to the treatment of living animals by the ballistic implantation of a biologically active material into a living animal body and the subsequent sustained release of the material. One aspect of the invention relates to a device adapted to penetrate the epidermal covering of a living animal body, lodge therein, and thereafter sustain release of a biologically active agent in situ in the living body. Another aspect of the invention relates to a ballistically implantable projectile which exhibits sustained release of a biologically active agent in response to contact with the tissues and fluids of a living body.

The successful management of wildlife and livestock herds requires the periodic adminstration of preventive medication and other treatments such as the administration of growth regulators, vitamins, and the like, at various stages throughout the growth cycle of the animals. The economic loss from sick or abnormal animals can be severe and such conditions must be minimized to maintain adequate profits in the raising of livestock.

It is the current practice in the livestock industry to inoculate animals at various stages throughout the growth cycle. This preferably occurs when the animals are young and may occur additionally at yearly or other intervals throughout the animals' growth cycle. These periodic treatments necessitate the gathering and treatment of the animals which is often a time-consuming and costly process, particularly in the case of large herds of animals such as cattle. Moreover, the capture or roundup of certain species of wildlife, such as mountain dwelling species, may be economically unsound or impossible. At the time of the roundup, particularly in the case of cattle, other body treatments such as shearing dehorning, branding, tagging, and multiple inoculations may be administered which can prove to be an excessive shock to the animal and result in the loss of some animals. Inoculations under physiological stress are often less effective than when applied to a relaxed animal and in fact the inoculation itself can cause disease in a stressed animal. Further, certain inoculations are most effective during particular periods during the animal's life cycle and should be administered during such periods rather than at unrelated, convenient periods such as at roundup.

Certain inoculations are also necessary to treat or provide immunity from contagious diseases such as anthrax. In these instances it may not be desirable to concentrate or round up the animals for administration and in any event the administration of such treatment may require elaborate precautions by the administrator to prevent contracting the disease from the animals.

The use of hypodermic syringes and injectors have been used for tranquilizing animals and various types of guns and other propulsion systems have been devised to deliver a hypodermic dart from a distance. Although these systems have proven effective, they are generally limited to delivery of liquids and further require the retrieval of the syringe for reuse.

In U.S. Pat. No. 3,616,758, a shell containing an immobilizing substance is shot at an animal and the shell ruptures upon impact to release the immobilizing substance, the shell fragments spreading into the surrounding tissue. Similarly, U.S. Pat. No. 979,993 teaches a ballistic device for tranquilizing animals which device includes a narcotic contained within openings in the projectile and, optionally, a gelatin covering protecting the narcotic or a suitable binder to retain or adhere the narcotic to the projectile during flight. In operation, the projectile is propelled into the flesh of the animal to be tranquilized. The gelatin is, on impact, physically displaced from covering the narcotic or is dissolved by the body fluids to release the narcotic and disable the animal. The projectile is removed from the animal or is made of a soluble substance so that it can be eliminated from the animal's system.

In order to overcome the need for the repeated capture and inoculation of live animals, the present invention provides a projectile which can be ballistically implanted in a living animal body from a convenient distance, and when implanted will remain in the body, without irritation, and provide sustained release of biologically active materials. As used in describing this invention, "sustained release" means continuous release or availability of a biologically active material over a prolonged period of time at a rate which is less than the rate of release of a "free" biologically active material of equivalent mass in the same physical form and in the same environment. Thus, the projectiles of this invention do not merely "dump" into or "flood" the body system with the entire amount of biologically active material, but provide a selected, sustained release of material at a rate which can be most effectively or efficiently utilized by the body. It is contemplated, however, that in certain embodiments of the invention "flooding" or quick release may be used with advantage in combination with sustained release of the biologically active materials as will be more fully described hereinafter.

The projectiles of the present invention can be used to provide sustained release of a variety of biologically active materials, e.g. vaccines or bacterins; growth promoters such as hormones, minerals or vitamins; antibiotics or other medicinal drugs. In some cases the projectile may contain a long term or lifetime supply of a particular or a plurality of materials such as minerals or vitamins, thereby precluding the need for a periodic roundup or capture and treatment of the animals and minimizing or eliminating the adverse physiological effects of administering multiple treatments and the added cost of said treatments.

The present invention comprises a ballistic projectile containing at least one biologically active material, the biologically active material being separated from the exterior of the projectile by a material which is capable of providing sustained release of the biologically active material when exposed to the fluids of a living animal body. Means for sustaining release of the biologically active material from the projectile can comprise an envelope, seal or matrix which is capable of retaining the biologically active material substantially sealed within the projectile during propulsion, inpact and nonlethal penetration of the projectile into an animal body and thereafter providing sustained release of the biologically active material into the body in response to exposure to the animal body fluids.

The sustaining means may operate by several known mechanisms. Thus, the sustaining means may comprise a matrix entrapping the biologically active material, which matrix dissolves in the body fluids and constantly exposes additional biologically active material to the body fluids. Alternatively, the sustaining means may be a microporous membrane or envelope which allows the transport therethrough of biologically active materials sealed thereby in response to a concentration or pressure gradient. Independent of whatever mechanism operates to sustain release of the agent, there is provided a unique, ballistically implantable projectile capable of providing sustained release of a biologically active agent when exposed to the body fluids of a living animal body.

DRAWINGS

The present invention can be made more clearly understood by referring to the drawings wherein several embodiments of the invention are shown.

FIG. 1 is a perspective view of one embodiment of a projectile casing adapted to receive a biologically active material, and FIGS. 2 – 5 are cross-sectional views of alternate embodiments of projectiles capable of providing sustained release of biologically active materials according to the present invention.

Referring to FIG. 1, there is shown a cylindrical, ballistic projectile 10 comprising a rounded nose 12 and annular walls 14 defining a generally cylindrical cavity 16 with an opening 18 at the base of the projectile. A ballast shown generally at 20 may optionally be included to modify the inflight characteristics of the ballistic projectile. This projectile is particularly suited to accept, retain, and release a biologically active material as will be more fully described hereinafter. Projectile 10 can be made of any material which is capable of being projected with sufficient force to penetrate a living animal body and which will maintain its dimensional stability and integrity on impacting and entering the animal body. Any of the numerous biomedically approved plastics can be used with advantage and can be chosen to be soluble or insoluble in the animal body. Exemplary of useful insoluble materials are the synthetic organic polymers such as the polyolefins, e.g., polyethylene and polypropylene; polysiloxane; polyamides, such as nylon; fluorinated hydrocarbon resins; ABS polymers (acrylonitrile-butadiene-styrene polymers) and the like. A suitable class of polymers which are soluble in animal bodies, e.g. cattle, are the cellulose derivatives such as hydroxypropyl cellulose, available commercially under the tradename "Klucel", Hercules Powder Co.

FIG. 2 shows a projectile 10 having rounded nose portion 12 and annular walls 14 defining a cavity 16 containing therein a biologically active material 22 which is shown for convenience as discrete particles in FIG. 2, but which could be provided as a solid block or plug or as a liquid. Agent 22 is sealed from the exterior of the projectile by sealing means 24 which is a microporous membrane which physically seals the biologically active material 22 from the exterior of the projectile while allowing the passage of the material, in solution, therethrough in response to a concentration or pressure gradient across the membrane 24. The microporous membrane can be any of the known microporous membranes such as the polymeric films having pores smaller than about 10 microns in diameter. Generally the pore size is between about 100 Angstroms and 10 microns for microporous membranes and about 7 to 50 Angstroms for ultrafilter types of membranes. Polymers such as cellulose, cellulose esters, epoxy resins, polypropylene, polyurethane, nylon, poly(vinyl-chloride), or polycarbonate are commonly used to prepare these membranes. For a more detailed discussion of these membranes and their preparation, reference is made to the "Encyclopedia of Polymer Science and Technology", Volume 8, John F. Wiley & Sons, New York (1968), pages 620–627. Other suitable microporous materials are prepared from polyolefin, amorphous resin, wax blends such as disclosed in German Laid Open Specification 2 019 724 (Hofacker) laid open Nov. 5, 1970.

FIG. 3 shows a projectile 10 with rounded nose portion 12 and annular walls 4 surrounding a matrix 26 capable of providing sustained release of a biologically active material 22 contained therein. Sealing cap 28 is optional and can be added for additional protection of the projectile contents during storage and launching if desired. Cap 28 can be made of a soluble material whereby the cap can dissolve in the animal body after being implanted and expose the matrix 26 to the animal body fluids. Cap 28 could also be made of a permeable material as is cap 24 of FIG. 2.

Alternatively cap 28 of FIG. 3 can be removably fastened to the projectile 10 in which case the cap can be removed prior to launching or can be constructed to separate from the projectile during launching, in flight or at impact prior to entering the animal body. A preferred embodiment comprises a cap 28 spot fastened to projectile 10 by adhesive means (not shown) whereby the force exerted on cap 28 during launching causes the cap to bow or buckle an amount sufficient to fracture the adhesive bond and release the cap after leaving the launching instrument, e.g., compressed air gun.

The release sustaining matrices of this invention are normally solid materials which are compatible with and non-irritating to living bodies and which operate in response to contact with animal body fluids and/or tissues to provide sustained release of a biologically active material contained therein. The matrix materials sustain release of the biologically active materials by slowly mobilizing in the presence of body fluids and tissues such as blood, fats, body enzymes or cells, and the like by degradation, dissolution, solvation, dispersion, or phagocytic mechanisms and the like, thereby slowly exposing and releasing the materials contained in the matrix, or by allowing the biologically active materials to be slowly leached from the matrix by the body tissues and fluids.

The matrix materials can be chosen to be specific to certain body fluids and tissues to supply biologically active materials to a localized area. The matrix materials can also be chosen to mobilize by a specific mechanism or to be more or less readily mobilized to provide for variation in the rate of release. Typical materials which have been found useful are proteins, such as gelatin; lipides, e.g., glycerides such as monostearin; natural waxes, e.g., animal waxes such as beeswax; cellulose derivatives, e.g., hydroxypropyl cellulose available commercially as "Klucel", Hercules Powder Co.; lactic acid salts, e.g., calcium lactate; and saccharides.

The projectile illustrated in FIG. 4 comprises a projectile 10 having annular walls 14 defining a compartmental cavity, the cells of which are indicated as **16*a* and 16*b* and which contain biologically active materials 22*a* and 22*b*, respectively. The cells are sealed by sealing means 30 and 32 which may be similar or different in chemical composition and function. Thus sealing means 30 may be readily soluble in body fluids to provide a quick release of material 22*b*, while seal 32 may comprise a microporous membrane to provide sustained release of material 22*a***. Alternatively, or additionally, materials 22a and 22b could be sealed in a release sustaining matrix material such as those described above to provide other desirable release programs. As can be appreciated, the projectile 10 may contain any number of compartments or cells in various forms, thus an embodiment wherein a plurality of cells are distributed longitudinally in the cavity and opening at the base of the projectile is also contemplated whereby a plurality of biologically active materials contained therein could be released simultaneously.

FIG. 5 illustrates a projectile 40 wherein all or only a portion of the nose 12, walls 14, and base 42 are formed from a release sustaining matrix material and wherein a biologically active material 22 is dispersed throughout the projectile. Cavity 16 is optional. Thus a solid projectile composed entirely of a release sustaining matrix material having biologically active material dispersed throughout the projectile is contemplated. Where the cavity 16 is included, additional biologically active materials can be included therein as shown in FIG. 5. These additional materials may be the same or different than the materials dispersed throughout the body of the projectile. Cavity 16 can also be filled or replaced with a "plug" of a release sustaining matrix which can be the same or different from the matrix material used in the remainder of the projectile.

In order to determine whether the projectiles of the present invention can provide sustained release in an animal body, in vitro testing in analogous biological environments can be performed. A method of making this determination involves involves preparing projectiles containing a biologically active material and release sustaining means and similar "control" projectiles containing the biologically active material without the release sustaining means for comparison. Sufficient amounts biologically active materials and in vitro test medium should be used so that the release of as little as 5 percent of the active material will result in readily detectable levels of active material in a sampled volume.

The projectiles containing the active material should be separately submerged in a small flask or tube containing from about 1 to 10 milliliters of the in vitro test medium. The containers should then be maintained at body temperature, e.g., about 37° C., and samples of the medium removed at intervals and assayed to determine the amount of active material released. The volume of sample removed should be as small as possible consistent with the sensitivity of the assay technique. The rate of sampling or the sampling interval will vary depending upon the release characteristics of the projectiles. Thus, the sample interval may be 30 or 60 minutes for the control projectile or other projectile which releases rapidly, or may be in the order of a day or more for projectiles which release slowly.

The time required to continuously release all or a given portion of the biologically active material is determined (beginning with initial release of the material when the initial release is delayed). A projectile provides "sustained release" if the time taken to release a given amount of the biologically active material from the projection is significantly greater than the time taken to release an equivalent amount from the "control".

The in vitro test media found to be suitable for the determination of "sustained release" comprise aqueous solutions compatible with the biologically active material and the release sustaining means. Specifically, these media are: distilled water; isotonic saline solutions (0.9 percent weight/volume sodium chloride); or buffered solutions such as Ringer's phosphate or phosphate buffered saline solution (0.5 molar sodium phosphate in isotonic saline, pH 7.0 – 7.4). Where the release sustaining materials are lipid-like matrix materials which are solubilized in the body by enzymatic action, e.g., glycerides or glycerol esters, pancreatic lipase (IUB code 3.1.1.3) should be included in the test media. Where the release sustaining matrices are proteinaceous in nature, a proteolytic enzyme mixture such as "Pronase" from *Streptomyces griseus* or "Protease" (Worthington Biochemical Corporation) should be added to the test media.

An alternative to in vitro testing involves implanting projectiles into the paravertebral muscle of rabbits. A sustained release projectile and a control can be implanted in a single animal and the comparison made as above. Results obtained in rabbits correlate well with results obtained in other animals.

As illustrated in the drawings, the projectiles of the present invention have been shown with recessed cavities generally cylindrical in nature, opening at the base of the projectile and defined by annular projectile walls. However, other recesses or cavities which vary as to location or shape can be utilized with advantage. Thus, cavities which are rectangular or triangular rather than rounded are contemplated as well as cavities which are straight, twisted, or constricted. Moreover, the cavities need not be provided with an opening at the base of the projectile and may extend transversely of the projectile with access at the sides or other portion of the projectile.

The projectiles of the present invention are adapted to be implanted into living animal bodies by ballistic means such as by launching or "shooting" the projectiles from a convenient distance with small arms or other launching devices powered by expanding gas means such as explosive charges or compressed gases, preferably air. When properly launched, the projectiles will penetrate a living animal body in a non lethal manner and come to rest within the body. The depth of penetration of the projectile can be controlled by balancing the relationship between the mass of the projectile and the velocity of the projectile at impact. The design of the projectile can vary and conventional designs useful herein are known in the art. The projectile design can be varied to achieve the desired degree of penetration into the body as well as to achieve the desired performance with respect to a wide range of impact velocities and a wide range of animals. Many texts are available to those skilled in the ballistics art which teach operative designs for the ogival and other portions of the projectile. See, for example, Hayes, "Elements of Ordnance", John Wiley and Sons, Inc., New York. It is generally preferred that the projectile have an elongated body with a tapered nose portion which may be rounded as shown in the accompanying drawings, conical or the like. A projectile design similar to that shown in the FIGURES of the drawings has been found effective for the intramuscular implantation of a 0.25 caliber projectile into the flanks of beef cattle at a distance of about 20 to 40 feet. The projectile should be capable of penetrating into and through the body tissue to the desired depth for maximum effectiveness depending on whether subcutaneous or intramuscular treatment is desired. The point at which entry into the living body is effected can readily be determined for maximum effectiveness utilizing minimum force.

When the projectile comes to rest within the animal body, the body fluids contact the sealing means to cause release of the biologically active material by penetrating, dissolving, degrading, softening or otherwise acting upon the means sealing the biologically active material in the projectile. The active materials in the projectile will be released continuously over a selected, prolonged period of time, thereby permitting a controlled and sustained entry of the biologically active material into the animal body.

The practice of the present invention can be further illustrated by reference to the following example.

EXAMPLE

Three Holstein calves were inoculated with vaccine-containing sustained release projectiles prepared according to this invention. The projectiles used in the inoculation were polypropylene projectiles having a conical nose portion and a cylindrical cavity opening at the base of the projectile. A small metal weight was placed in the forward end of the cavity as ballast and fastened therein with an epoxy resin. Each projectile weighed approximately 0.7 grams gross weight and included a vaccine sealed in a release-sustaining matrix. The projectiles were loaded with vaccine as follows:

A 10 dose vial of infectious bovine rhinotracheitis (IBR) vaccine (modified live virus vaccine, "Anchor IBR-VAC", Anchor Laboratories, Inc.) was reconstituted with 0.5 ml of a 5% aqueous hydroxypropyl cellulose ("Klucel", Hercules Powder Co.) solution. Aliquot samples containing 0.05 ml of the vaccine were placed in the projectile cavities and lyophillized (freeze dried) in the cavity. A small circular polycarbonate disc (0.25 inch diameter × 10 mils thick) was placed over the cavity opening at the base of the projectile and lightly heat sealed to the projectile base for protection prior to and during launch.

A 0.25 caliber air powered rifle was used to propel the projectiles at the large neck muscle in the upper portion of the neck of each of the calves from a distance of about 20 feet. The projectiles exited the air rifle with a muzzle velocity of about 900 feet per second. The protective disc was broken loose from the projectile during the launching of the projectile. The projectiles penetrated the necks of the calves and lodged in the muscle tissue at a depth of about 1 to 2 inches beneath the skin.

Blood samples were taken from the calves prior to implantation of the vaccine-containing projectiles and periodically after implant. The blood samples were assayed for IBR virus neutralizing antibody by a serum neutralization technique. By the 14th day following implantation, significant titers of virus neutralizing antibody were found in all three calves. The antibody titers in the calves rose to levels which would normally be considered as protective against IBR challenge.

What is claimed is:

1. A means for providing controlled sustained release of a biologically active material comprising a ballistic implant shaped for ballistically penetrating the epidermal covering of a live animal body and lodging totally within the tissues of the animal body, said implant comprising a ballistic-shaped, biologically compatible polymer body containing therein at least one biologically active material, said biologically active material being separated from the exterior of said ballistic implant by a material defining a means for providing controlled sustained release of said biologically active material to the tissue of the animal body when exposed to the fluids and cells of said living animal body.

2. A ballistic implant according to claim 1 wherein said biologically active material is distributed within a release sustaining matrix of material which is soluble in the fluids of a living animal body.

3. A ballistic implant according to claim 2 wherein said release-sustaining matrix is carried in a cavity opening to the rear of said ballistic implant.

4. A ballistic implant according to claim 2 wherein said release-sustaining matrix consists essentially of an organic compound selected from the group consisting of gelatin, hydroxypropyl cellulose, glycerides, and beeswax.

5. A ballistic implant according to claim 1 wherein said biologically active material is at least partially enclosed by a material which is insoluble in, but permeable to the fluids of a live animal body.

6. A ballistic implant according to claim 5 wherein said insoluble, permeable material is a microporous membrane.

7. A ballistic implant according to claim 1 wherein said polymer body comprises a plastic material.

8. A ballistic implant according to claim 1 wherein said polymer body is soluble in the fluids of a living animal body and said biologically active material is distributed throughout the said polymer body.

* * * * *